(12) United States Patent  (10) Patent No.: US 8,096,807 B2
Benfield et al.  (45) Date of Patent: Jan. 17, 2012

(54) DENTAL INSTRUMENTATION UNIT

(75) Inventors: Tom Benfield, York, SC (US); Joe Bria, Waxhaw, NC (US); John Helgesen, Rock Hill, SC (US); Austin Unsworth, Fort Mill, SC (US)

(73) Assignee: Dental Equipment, LLC, Charlotte, NC (US)

( * ) Notice: Subject to any disclaimer, the term of this patent is extended or adjusted under 35 U.S.C. 154(b) by 90 days.

(21) Appl. No.: 12/563,190

(22) Filed: Sep. 21, 2009

(65) Prior Publication Data

US 2010/0129770 A1 May 27, 2010

Related U.S. Application Data

(60) Provisional application No. 61/117,209, filed on Nov. 23, 2008.

(51) Int. Cl.
*A61C 15/00* (2006.01)
(52) U.S. Cl. ............................................ 433/77; 433/92
(58) Field of Classification Search .................... 433/49, 433/53, 77, 78, 79, 91, 92
See application file for complete search history.

(56) References Cited

U.S. PATENT DOCUMENTS

| | | | | |
|---|---|---|---|---|
| 3,484,941 A * | 12/1969 | Svard | | 433/92 |
| 4,386,910 A * | 6/1983 | Cattani | | 433/92 |
| 5,127,830 A * | 7/1992 | Sheridan et al. | | 433/77 |
| 5,997,297 A * | 12/1999 | Coburn et al. | | 433/77 |
| 6,692,253 B2 * | 2/2004 | Brockway et al. | | 433/77 |

* cited by examiner

*Primary Examiner* — Ralph Lewis
(74) *Attorney, Agent, or Firm* — Timothy H. Van Dyke; Beusse, Wolter, Sanks, Mora & Maire, P.A.

(57) ABSTRACT

An instrumentation delivery unit which supports hand-held dental instruments. In one example first and second housing members form a sealed chamber. When the members are separated, access is permitted to the interior of the chamber, e.g., for maintenance purposes. A first portal suitable for connection to a vacuum line provides a partial vacuum in the chamber, and second portals provide connection via second vacuum lines between the chamber and dental devices to operate the devices. The housing includes hand piece holders each of an initial diametric size for receiving hand pieces up to a maximum diametric dimension, with one of the hand piece holders formed along two adjoining ones of the housing members. The adjoining housing members secure inserts between one another to provide a second diametric size smaller than the initial diametric size to thereby selectably accommodate hand pieces having a smaller diametric dimensions.

15 Claims, 7 Drawing Sheets

DENTAL INSTRUMENTATION UNIT

RELATED APPLICATION

This application claims priority to provisional patent application U.S. 61/117,209, filed 23 Nov. 2008 which is incorporated herein by reference in the entirety.

FIELD OF THE INVENTION

This invention relates to dental operating equipment, and in described embodiments, relates more particularly to instrumentation units enabling interchangeability of equipment or convenient maintenance by a dental assistant.

BACKGROUND AND SUMMARY OF THE INVENTION

Dental delivery systems are often configured with a series of holders into which hand pieces are placed for storage. The holders are normally slotted, each in the shape of a half circle or half cylinder that has an opening slot suitably sized to assure that the hand pieces can be placed in the holders. Commonly, the hand pieces are connected to supplies such as a water line, a pressurized source of air and partial vacuums. Other hand pieces may be electrically powered. Prior arrangements of holders and hand pieces have typically been of fixed design. For example, it is common for a delivery system to be configured for a typical user without an ability to customize to the needs of a particular procedure or to the preferences of a specific user. Further, even to the extent a system is suitable for one user, e.g., dental assistant, such systems are not readily convertible to easily accommodate users with different needs or preferences such that two or more persons may use the same unit, each with optimal convenience. Embodiments of the present invention provide for a dental assistant's unit which supports hand-held instruments used in dental procedures and that allows for interchangeability of instruments or for convenient cleaning of the unit by a user.

In accord with a first exemplary embodiment of the invention, there is provided an instrumentation delivery unit of the type which supports hand-held instruments used in dental procedures. A housing includes a plurality of member components which are collectively configurable in an open position and a closed position. For example, first and second members, when configured in the closed position, provide a sealed chamber and, when configured in the open position, permit access to the interior of the chamber. The chamber includes a first port suitable for connection to a vacuum line to create a partial vacuum in the chamber. At least a second port provides a connection via a second vacuum line between the chamber and a first hand-held instrument to operate the instrument when a partial vacuum is applied through the second vacuum line. The housing includes, along an exterior portion thereof, a series of hand piece holders. One or more of the holders are suitable for releasably holding the first hand-held instrument when the device is not in operation. The first and second member components include a fastening mechanism for releasably holding the members together when the housing is configured in its closed position and enabling separation of the members to permit access to the interior of the chamber when the housing is configured in the open position.

In accord with a second exemplary embodiment of the invention, an instrumentation delivery unit, also of the type which supports hand-held instruments for use by a dentist or dental assistant in performing dental procedures via the use of the hand-held instruments, includes a housing adapted to be supported by a dental delivery arm in a position adjacent a dental chair also formed of a series of member components configurable in multiple positions. A series of hand piece holders are formed long an exterior portion, e.g., surface, of the housing. Each holder is of an initial diametric size (which size may vary among different holders) for receiving hand pieces up to a maximum diametric dimension. One or more of the hand piece holders is formed along two adjoining ones of the housing members, and with each such hand piece holder formed by two adjoining housing members an insert can be secured therebetween. With the insert so secured, the holder in combination with the insert provides a second diametric size smaller than the initial diametric size of the holder, and the invention enables selectable accommodation of hand pieces having a maximum diametric dimension smaller than the initial diametric size of the holder. By way of example, the hand pieces may be hand-held instruments of the types used in a variety of dental procedures, including instruments that operate based on vacuum forces or on electrical power. One of the housing members may be manually removable to enable an assistant to modify an arrangement of several such inserts by repositioning inserts for individual holders between the adjoining housing members, i.e., pairs of housing members may be configured to secure multiple inserts between one another.

In a described embodiment, such an instrumentation delivery unit includes a housing wherein, when first and second housing members are brought together, a sealed chamber is formed therein and, when separated, access is permitted to the interior of the chamber, e.g., for maintenance purposes. The exemplary chamber includes a first portal suitable for connection to a vacuum line to create a partial vacuum in the chamber, and at least a second portal providing a connection via a second vacuum line between the chamber and a first dental device, e.g., a hand held instrument, to operate the device when a partial vacuum is extended through the second vacuum line. The housing includes, along an exterior portion thereof, a plurality of hand piece holders each of an initial diametric size for receiving hand pieces up to a maximum diametric dimension, with one of the hand piece holders formed along two adjoining ones of the housing members. The two adjoining housing members are configured to secure one or more inserts between one another to provide a second diametric size smaller than the initial diametric size and thereby selectably accommodate a hand piece having a smaller than maximum diametric dimension. Multiple such inserts may be of varied size diametric sizes, each interchangeably positionable in multiple ones of the hand piece holders.

BRIEF DESCRIPTION OF THE DRAWINGS

The invention will be better understood from the following description taken in conjunction with the accompanying drawings wherein.

Like reference characters denote like or corresponding parts throughout the figures. In order to emphasize certain features relating to the invention, certain features shown in the figures may not be to scale.

DETAILED DESCRIPTION OF THE INVENTION

Before describing in detail the particular methods and apparatuses related to embodiments of the invention, it is noted that the present invention resides primarily in a novel and non-obvious combination of components. So as not to obscure the disclosure with details that will be readily apparent to those skilled in the art, certain conventional components (e.g., air and water supply lines) have been omitted or presented with lesser detail, while the drawings and the specification describe in greater detail other elements and steps pertinent to understanding the invention. Further, the following embodiments do not define limits as to structure or method according to the invention, but only provide examples which include features that are permissive rather than mandatory and illustrative rather than exhaustive.

Figure 1:
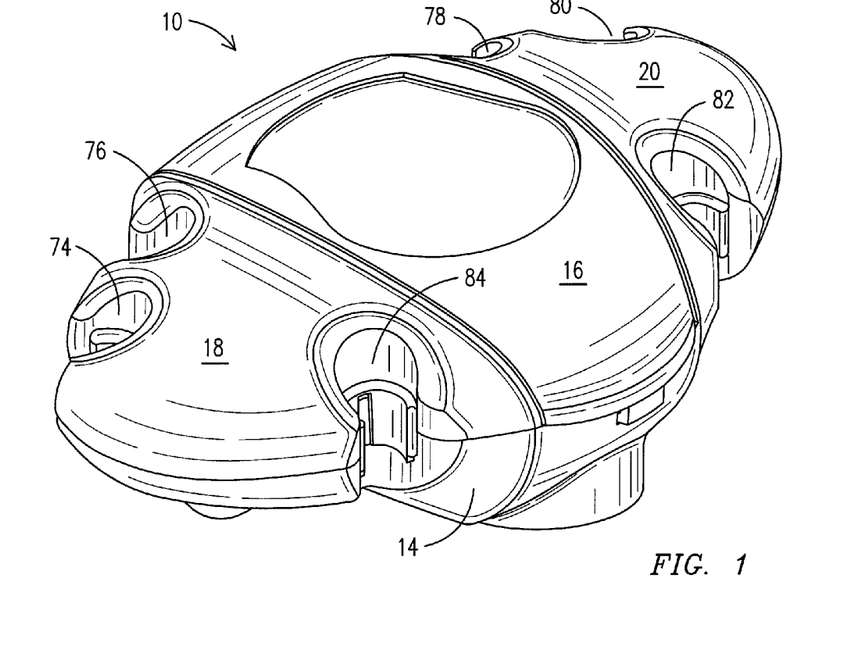
FIG. 1 is a perspective view of an instrumentation delivery unit of the type which supports hand-held instruments such as used in dental procedures.
Figure 2:
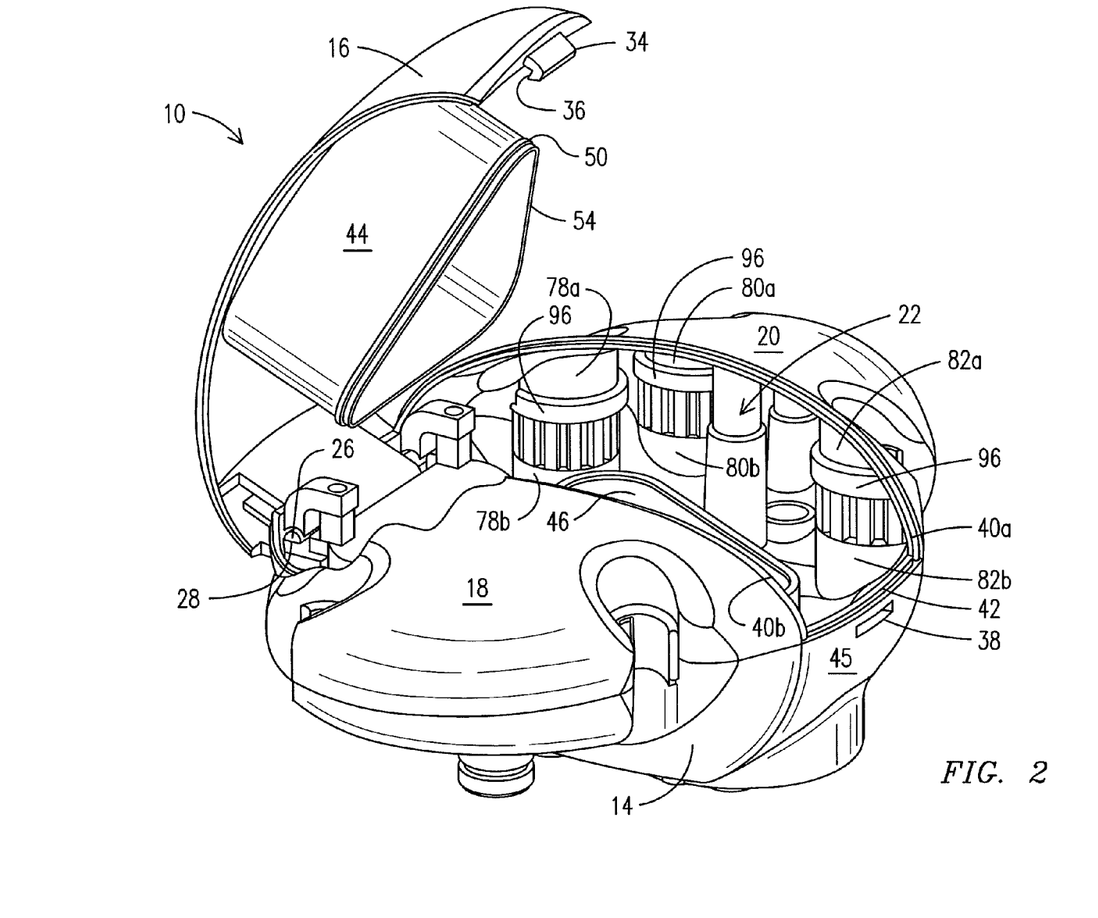
FIG. 2 is another perspective view of the instrumentation delivery unit shown in FIG. 1, illustrating features observable when the unit is in an open position.
Figure 3:
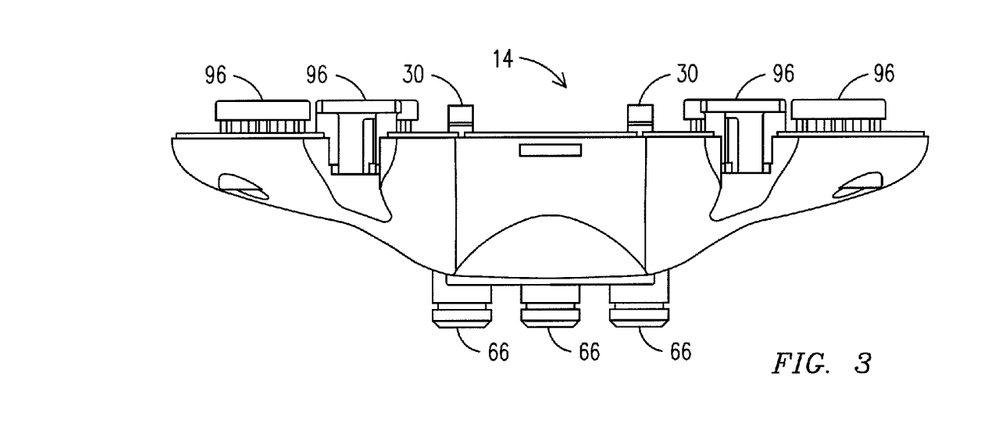
FIG. 3 is a front elevation view of a lower member of the unit shown in FIG. 1 with numerous components attached thereto.

With reference to FIGS. 1 and 2, there is shown an instrumentation delivery unit 10 of the type which supports handheld instruments such as used in dental procedures. The unit 10, shown to have an oblong, somewhat elliptical shape, comprises multiple housing members and attachments. The illustrated unit comprises a base member 14, (also shown in FIG. 5) over which are positioned a central upper housing cover 16 and two other upper housing members 18, each positioned along a different side of the central upper housing cover 16. The central upper housing cover 16 is rotatably attached to the base member 14 to provide an arrangement wherein the cover 16 may be placed in an open position to provide access through an opening 22 into the unit 10 and in a closed position against other members of the unit.

Figure 4:
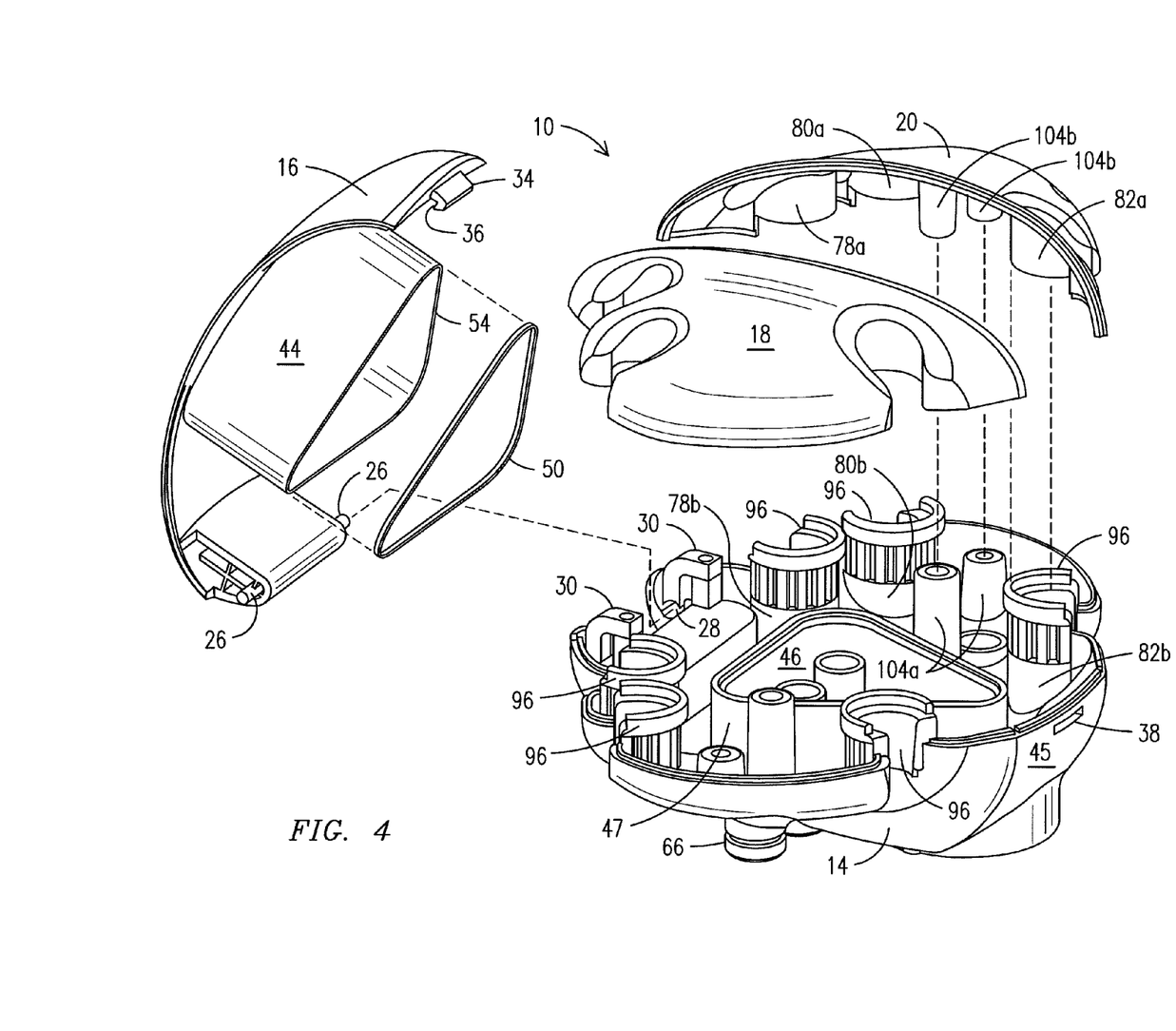
FIG. 4 is an exploded view of the unit shown in FIG. 1.

The base member 14, the cover 16 and the other upper housing members 18 and 20 each include numerous features which may be integrally formed during manufacture of the respective component, e.g., with injection molding or another common casting process. For example, to provide a hinge-like means of attachment, with which the central upper housing cover 16 may swing between open and closed positions, the cover 16 includes a pair of protruding hinge pins 26 which may be integrally formed with the cover 16 as shown in FIG. 4. The hinge pins 26 are each insertable into an aperture 28 formed in one of a corresponding pair of hinge posts 30 formed on the base member 14. In the illustrated embodiment, the posts are integrally formed along a rear portion 32 of the base member 14. See, also, FIG. 5. With this arrangement the cover 16 may be placed in a closed position resting along adjacent edges which define the opening 22, i.e. edges 40*a*, 40*b* along the two other upper housing members 18, 20 and edge 42 along an upper surface of the base member 14. The central upper housing cover 16 may be rotatably displaced via the hinge pins 26 and posts 30, from the closed position as shown in FIG. 2 to the open position shown in FIG. 1. Operation of the housing arrangement of the members 14 and 16 may be effected with any of multiple other hinge designs, including snap-on arrangements which permit complete removal of the central upper housing member 16 from the base member 14.

The upper housing cover 16 and the base member 14 include mating latch members to tightly secure the cover 16 against the base member in a closed position. The cover 16 includes a resilient latch tongue 34 having a catch portion 36 which can be snapped into a suitably shaped opening 38 when the cover 16 is urged into a closed position. The opening 38 is positioned along an upper exterior surface 45 of the base member 14 and a sufficient distance below the edge region 42 to assure that, when the opening 38 receives the catch portion 36, the cover 16 fits tightly against the base member 14. Also, as further described herein, when the cover 16 is in the closed position, this arrangement imparts a desirable amount of pressure between each of the cover 16 and base member 14 and an intervening seal to enable a chamber formed within the housing 10 to sustain a desired partial vacuum. The latch tongue 34 can be released from the opening 38 by applying a modest upward force to the cover 16 which sufficiently flexes the cover 16 to displace the catch portion 36 out of the latch opening 38 and allow upward movement of the cover 16 away from the latch opening 38.

A feature of the unit 10 is that when the central upper housing cover 16 is in a closed position with respect to the base member 14, a sealed vacuum chamber is formed within the enclosed volume of the unit. The vacuum chamber is formed as two separable components 44 and 46. A lid component 44 serves as a removable cover which is formed along an inner surface of the central upper housing member 16. A vessel component 46, formed along an inner surface 48 of the base member 14, as shown in FIGS. 4 and 5, serves as a vessel for receiving liquid and debris collected during dental procedures. The lid component 44 is positionable over and about the vessel component 46 to press against the inner surface 48 of the base member 14. The lid component 44 includes a seal 50 positioned along the distal edge region 54. When the central upper housing cover 16 is in a closed position over the opening 22, the edge region 54 and the seal 50 of the lid component 44 press against the inner surface 48 of the base member 14. In this configuration, the lid component 44, with the seal 50 pressed between the edge region 54 and the inner surface 48, encloses wall portions 47 of the vessel component 46 extending above the inner surface 48 of the base member 14. See FIG. 7. This arrangement effects a sufficiently air tight assembly to sustain a partial vacuum in the closed chamber 44/46.

Figure 5A:
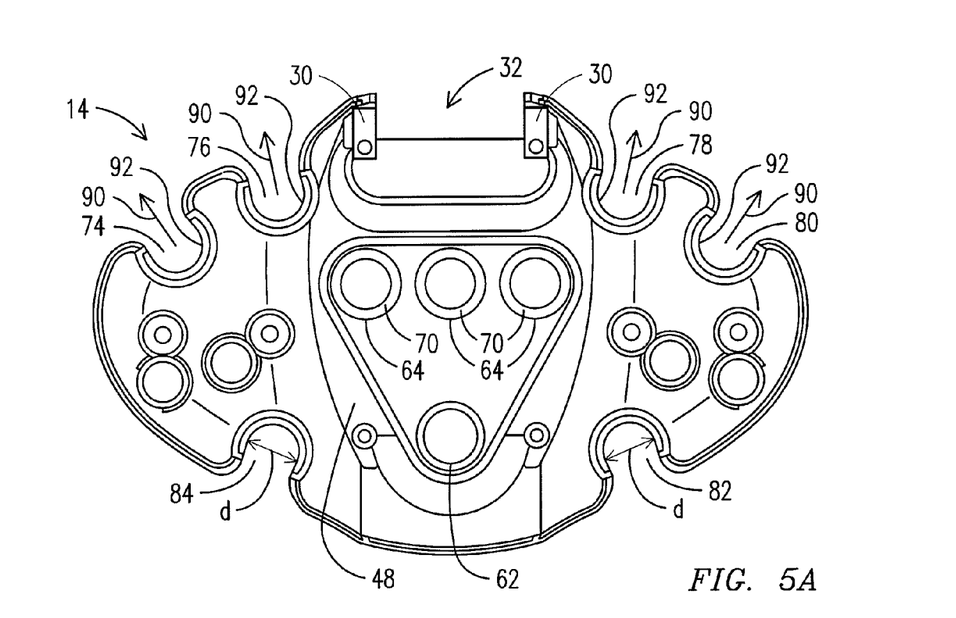
FIG. 5A is a first elevation view of the lower member shown in FIG. 3.
Figure 5B:
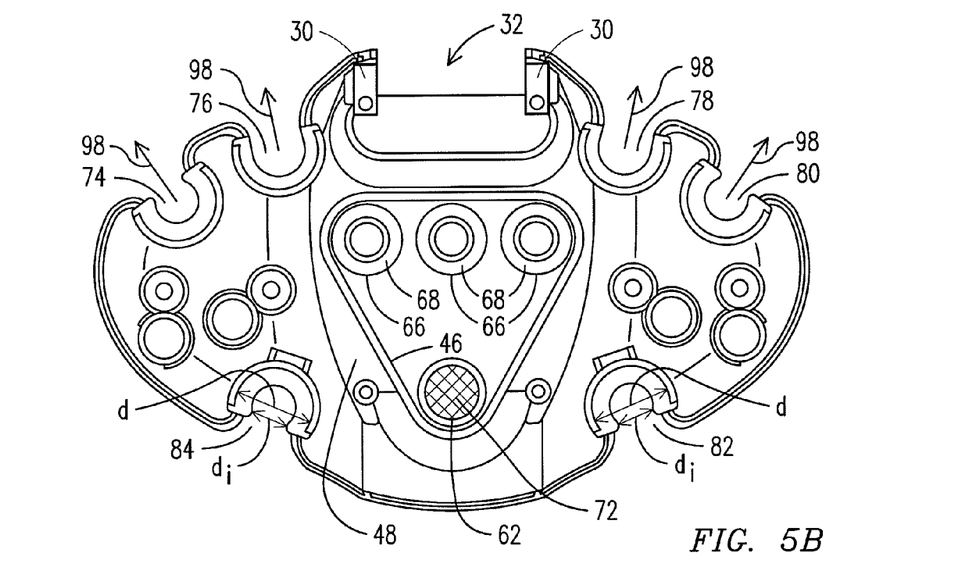
FIG. 5B is another elevation view of the lower member shown in FIGS. 3 and 5A wherein numerous other components of the unit are incorporated.

The base member 14 includes a series of ports which extend into the vessel component 46 of the chamber. See FIGS. 3-7. A main vacuum portal 62, shown in the plan views of FIGS. 5A and 5B, is connectable through a main vacuum line 63 as illustrated in FIG. 8. The line 63 is connected to a pump (not shown) to provide the source for the partial vacuum in the chamber when the lid component 44 is pressed into a sealing engagement against the inner surface 48 of the base member 14.

Figures 6A, 6B:
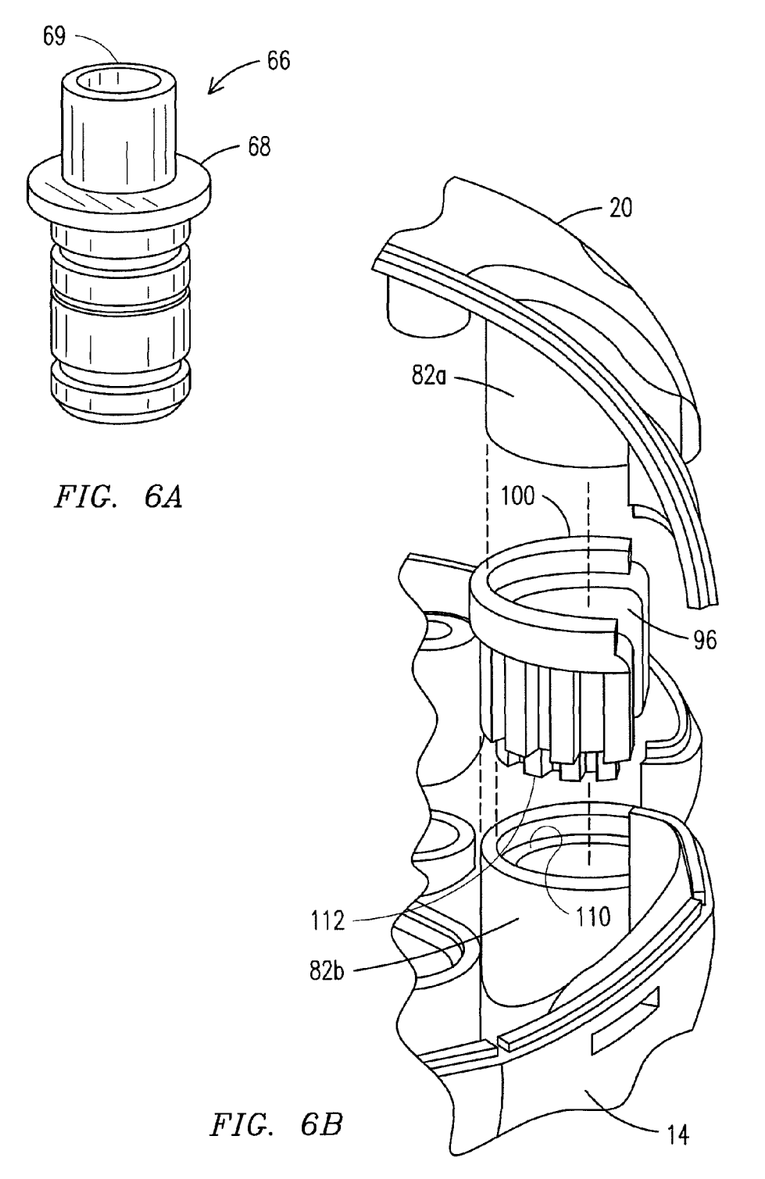
FIG. 6A is a perspective view of an exemplary design for a vacuum line connector also shown in FIGS. 3-5.
FIG. 6B is a exploded perspective view of a portion of the unit shown in FIGS. 1, 2 and 4 illustrating an exemplary design for an insert useful for modifying the size of an opening of hand piece holders formed on the unit as shown in FIGS. 1, 2 and 4.
Figure 7:
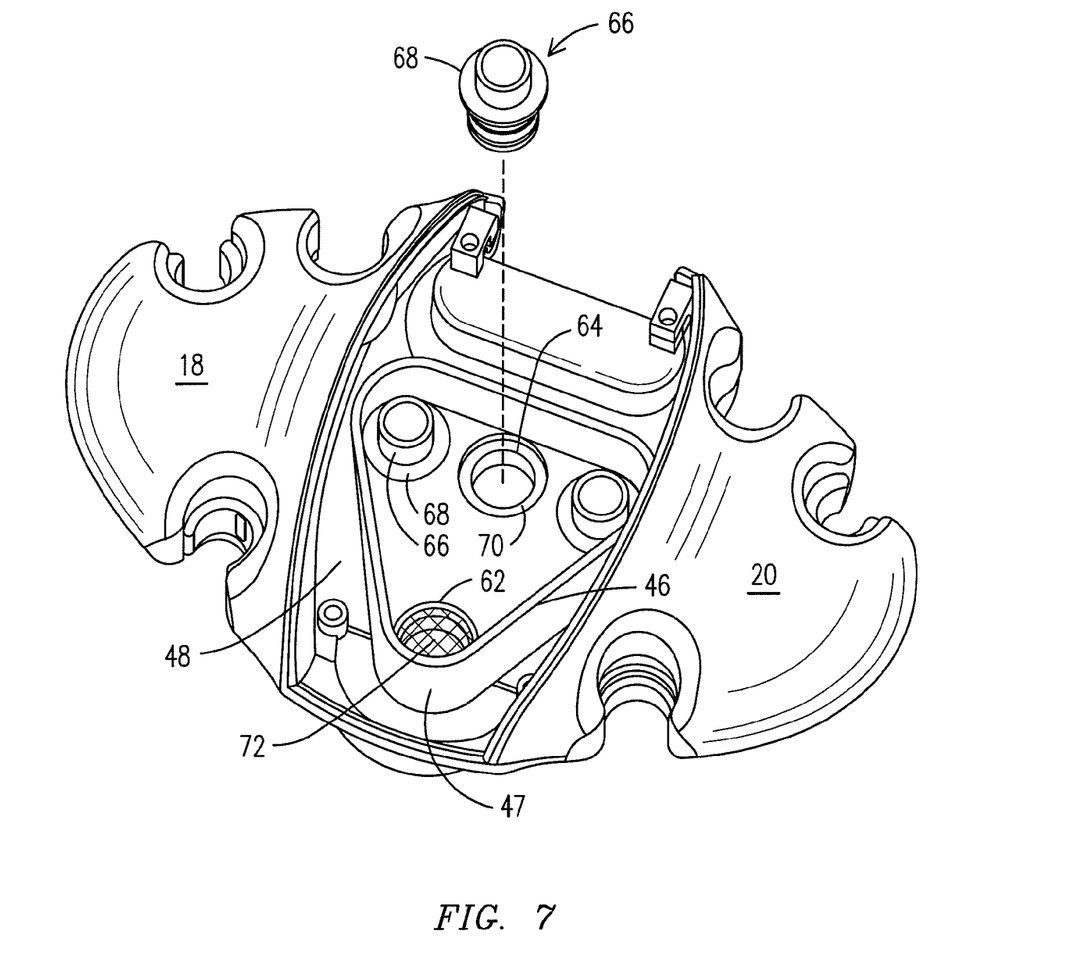
FIG. 7 is a perspective view of the unit shown in FIGS. 1 and 2 with a cover removed, illustrating component features of the unit.
Figure 8:
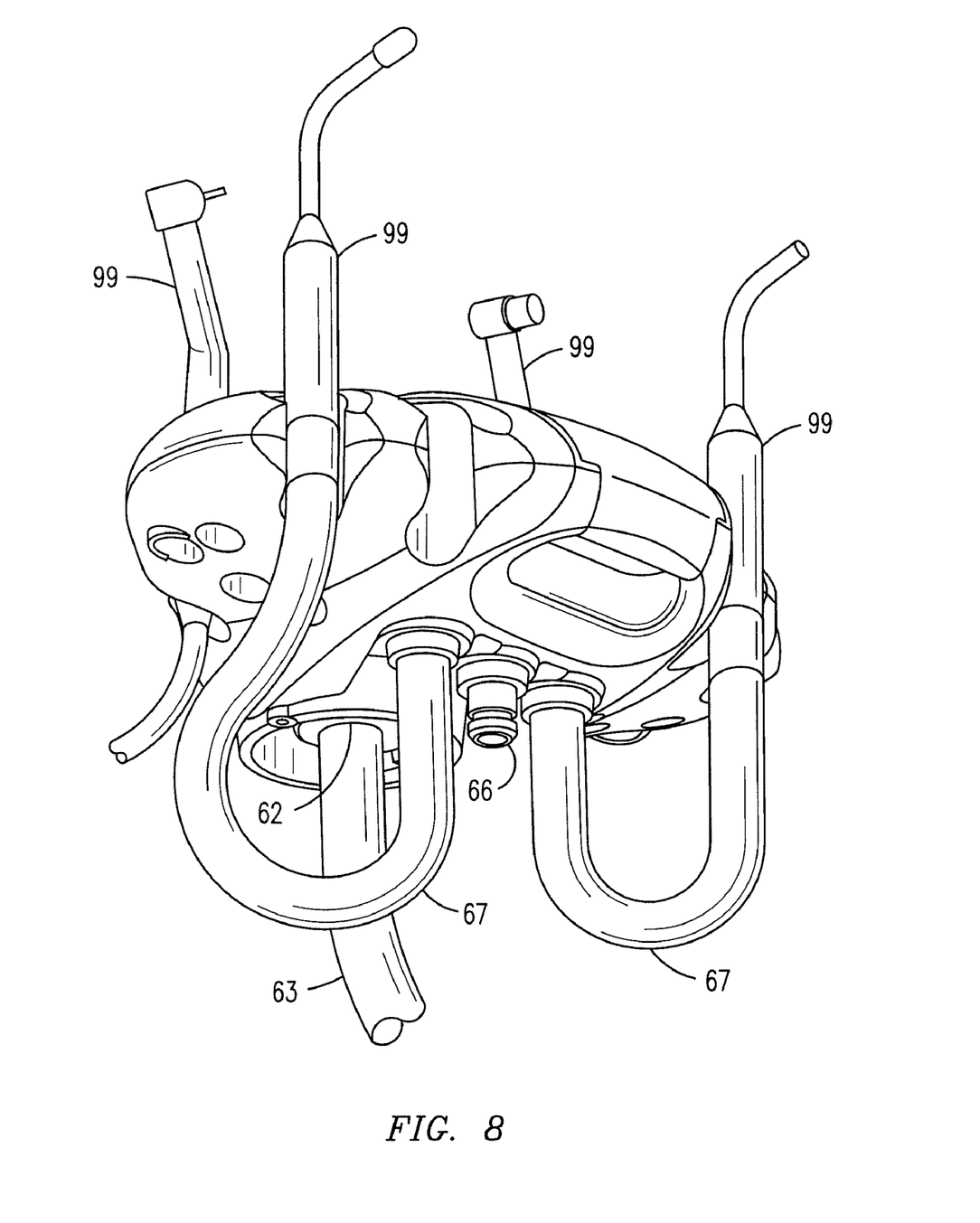
FIG. 8 is a perspective view of the assembled unit incorporating exemplary dental instruments and vacuum lines attached in accord with the invention.

Also with reference to FIGS. 5 and 7, the chamber further includes three exemplary instrument line portals 64 within the vessel component 46 and positioned along the inner surface 48 of the base member 14. As shown in FIGS. 5B and 6A, vacuum line connectors 66 are attached to the base member 14 through each portal 64 for delivery of a vacuum force via a secondary vacuum line 67 to an instrument 99 or other dental device. See, again, FIG. 8. The exemplary vacuum line connector 66 shown in the perspective view of FIG. 6A has a generally cylindrical shape with an intermediate washer-shaped rim 68 of greater diameter than the general cylindrical shape. The rim 68 is positioned adjacent an upper end 69 of the cylindrical shape to facilitate securement of the connector 66 in a portal 64. With a washer-shaped recess 70 formed about each portal and along the inner surface 48, the rim 68 is sized to fit snugly within the recess to stabilize the position of the connector 66. See, also, FIG. 7. Various arrangements of seals (not shown) may be incorporated in the connectors 66 to sustain partial vacuum conditions.

A filter element is positioned in the flow path leading from the instrument line portals 64 into the main vacuum portal 62 to prevent debris which may enter the chamber through one of the portals 64 from exiting the vessel through the main vacuum portal 62. The filter element is schematically shown as a simple screen 72 in FIG. 5B, but it is to be understood that other well known filter designs can be employed to trap debris while permitting vacuum flow to travel into the main portal 62.

The instrumentation delivery unit 10 further includes a series of hand piece holders 74, 76, 78, 80, 82 and 84 positioned along the periphery of the unit 10. The holders are recesses or slots in the shapes of half cylinders which each extend along an upper member 18 or 20 and along the base member 14. Having half cylinder shapes, the holders are each capable of accommodating tools of varied diametric sizes which may be slid into the slot. By diametric size it is meant that, with hand held dental instruments typically being of an elongate but often irregular profile, and having an associated thickness or girth which may vary, the instruments each have an associated diametric-like dimension which corresponds to the diameter of an elongate, regular cylindrically shaped body. With this understanding, it will be apparent from the figures that each of the hand piece holders provides a slot formed with a characteristic diametric size suitable to receive a dental instrument having a corresponding diametric feature up to a like dimension. The hand piece holders 74, 76, 78, 80, 82 and 84 are each schematically shown in the plan view of FIG. 5A as a half-cylinder shape having a diameter d and positioned so that the open portions (i.e., the slots) indicated by arrows 90 face outward from the unit 10 to receive instruments 99 having thicknesses up to that same diameter.

With the unit 10 formed in multiple components, including the upper members 18, 20 and the base member 14, a feature of the invention is that the holders 74, 76, 78, 80, 82 and 84 can be formed as sleeve-like receptacles each comprising two connectable sections: 74a, 74b; 76a, 76b; 78a, 78b; 80a, 80b; 82a, 82b; and 84a, 84b. The perspective views of FIGS. 2 and 4 illustrate features of the holders 78, 80 and 82, which features are also common to the holders 74, 76, and 84. Interior portions of the housing member 20 and the base member 14 are viewable with the instrument delivery unit 10 in the open position shown in FIG. 2. As shown in this view, and the view of FIG. 6B, the holder 82 comprises an upper section 82a, formed as part of the housing member 20, and a lower section 82b formed as part of the base member 14. The sections 82a and 82b are connectable to one another through an insert 96 (see also FIG. 4) which reduces the size of the hand piece holder from the diameter d to accommodate instruments having thicknesses smaller than the diameter d with a close or snug fit for secure placement of an instrument through the slot of the holder 78. With each of the holders 74, 76, 78, 80, 82 and 84 formed with two separable sections (e.g., 78a, 78b; 80a, 80b, etc.) such inserts 96 may be interposed between the two sections. Accordingly, the inserts 96 can be selected based on diametric size to selectively alter and customize the maximum diametric dimensions of each slot-shaped hand piece holder 74, 76, 78, 80, 82 and 84. The exemplary design for such an insert 96, shown in the perspective view of FIG. 6B, comprises a body generally in the shape of a half cylinder suitably sized to fit concentrically within one of the holders 74, 76, 78, 80, 82 and 84. When installed in a holder, an open portion of each insert, indicated in FIG. 5B with arrows 98, extends outward from the unit 10, more or less aligned with the open portion 90 of the holder so that pairs of open portions 90 and 98 are aligned to receive instruments having thicknesses $d_i$ which range up to about the inside diameter of the insert 96. See FIG. 5B. In FIG. 8 a series of instruments 99 are shown installed in the holders 74, 76, 78, 80, 82 and 84.

A major outside surface 97 of the inserts 96 has an outer diameter substantially the same as the diameter "d" of the hand piece holder 74, 76, 78, 80, 82 or 84 into which it is inserted.

Each of the inserts 96 includes along an upper end a shoulder 100 which is sufficiently greater than d such that when the shoulder 100 is positioned between the separable upper and lower sections (e.g., 82a, 82b) of a holder, the shoulder 100 can be nested against the upper section (e.g., 82a). The lower sections of the holders (e.g., 82b) each include at an upper end a shoulder 110 including a recessed ridge with the shoulder 110 having a diameter sufficiently greater than a lower portion 112 of an insert 96 so that when the lower portion 112 of an insert is positioned in the shoulder it can be nested against the lower section (e.g., 82b). With this arrangement of inserts positioned between upper and lower holder sections, the upper members 18, 20 can be fastened to the base member 14 in order to secure the nested inserts 96 in place. Numerous fastening means are suitable to assemble the unit and secure the holders. For example, a series of hollow base posts 104a (shown in FIG. 4) may be formed in the base member 14 for alignment with posts 104b in one of the upper members 18, 20 having threaded blind holes (not shown) so that a screw may extend through each base post 104a and be turned in a blind hole for fastening to a post 104b. With a suitable fastening arrangement, the shoulders 100 and 110 are clamped against opposing ends of each insert 96 to secure the insert. A feature of this arrangement is that a user of the unit can easily disassemble components to interchange inserts 96 of different inner diametric sizes in order to receive instruments having different thicknesses $d_i$ which range up to about the inside diameter of the insert 96. With inserts of varying sizes accommodating dental instruments 99 of different thicknesses, the effective sizes of the holders 74, 76, 78, 80, 82 and 84 can be readily customized as needed by users on a day-to-day basis or even more frequently.

A feature of the invention is provision of multiple inserts 96 having different diametric dimensions (e.g., interior diameters) for receiving hand tools of varied diametric dimension. Although the hand piece holders are illustrated as being of uniform dimensions, they may be manufactured with different diametric dimensions. Thus, while the hand piece holders may be formed of identical, or different, diametric dimensions, inserts 96 may be customized to fit among the like or dissimilar hand piece holders 70, 72, 74, 76, 78 and 80 and also provide differing receiving diameters (i.e., diametric dimensions) suitable for specific hand tools of different sizes.

This customization enables the unit 10 to be fitted for varied combinations of differently sized hand tools, and also affords the dental specialist a flexibility to rearrange configurations of hand piece holders according to personal preferences. For example, two persons may have different preferences with respect to the location of specific hand tools. The preferences may be based on whether a specialist is right handed or left handed, or may be based on specialization of work and the frequency with which certain tools are used. The upper side members 18 and 20 may be removed from the base member by various means. For example, the members may be fastened to the base member with screws, or the members 18 and 20 with the base member 14 may incorporate multiple mating latch members such as described herein for securement of the cover 16 with a latch tongue 34 having a catch portion insertable within a latch opening. In lieu of a hinged relation such as described for the cover 16, the members 18 and 20 may be secured to the base member 14 with pairs of mating latch members which can be released by exerting small squeezing forces upon the members 18 and 20 to release the catch portions from the base member. This simple, manual release means enables an assistant to easily modify an arrangement of inserts 90 based on tool preferences and preferred locations.

An embodiment of a dental instrumentation delivery unit has been described. In one series of embodiments the unit includes a housing with multiple members that are configurable in multiple positions. For example, first and second members, when brought together in a closed position, provide a sealed chamber inside the unit and, when separated in an open position, permit access to the interior of the chamber for purposes of removing debris and for maintenance. The chamber includes a main port suitable for connection to a vacuum line to create a partial vacuum in the chamber. Multiple second ports may each provide connections via second vacuum lines between the chamber and a dental instrument 99 to operate the dental instrument when a partial vacuum is extended through the second vacuum line. The housing may include, along an exterior periphery thereof, a plurality of hand piece holders. The holders are suitable for reversibly holding dental tools when each of the tools is not operating. To effect provision of a partial vacuum in the chamber, the first and second members may be coupled to one another in a hinged arrangement so that the members may be separated to permit access through an opening to the interior of the chamber. With respect to an embodiment having a hinged arrangement, the access is effected by rotation of the first member with respect to the second member. In one embodiment, the chamber is formed with a lid portion, positioned along an interior surface of the first member, and a vessel portion, positioned along an interior surface of the second member to receive the lid portion in a sealing relationship to sustain at least a partial vacuum. The sealing relationship may be had by pressing a seal between the lid portion and an interior surface formed along the second member.

In another series of embodiments, a customizable dental instrumentation delivery unit supports a variety of hand-held instruments of differing sizes and shapes for use in dental procedures. A housing includes a plurality of members configurable in multiple positions. The housing includes, along an exterior periphery thereof, a plurality of hand piece holders, each having an initial diametric size for receiving hand pieces up to a maximum diametric dimension. One of the hand piece holders is formed along two adjoining ones of the housing members and the two adjoining housing members are configured to secure an insert along an interface between the two adjoining housing members. Such positioning of the insert provides the holder with a second diametric size smaller than the initial diametric size and permits selectable accommodation of differing hand pieces each having a smaller than maximum diametric dimension.

While the invention has been described with reference to particular embodiments, it will be understood by those skilled in the art that various changes may be made and equivalents may be substituted for elements thereof without departing from the scope of the invention. The scope of the invention is only limited by the claims which follow.

The claim invention is:

1. A dental instrumentation delivery unit of the type which supports hand-held instruments for use by a dentist or dental assistant in performing dental procedures via the use of a hand-held instrument, comprising:
   a housing to be supported by a dental delivery arm in a position adjacent a dental chair and including a plurality of members configurable in an open position and a closed position;
   the housing including first and second members which, when configured in the closed position, provide a sealed chamber therein and, when configured in the open position, permit access to an interior portion of the chamber, and the housing including, along an exterior portion thereof, a plurality of hand piece holders each of a first diametric size for receiving hand-held instruments up to a maximum diametric dimension;
   the chamber including a first port suitable for connection to a vacuum line to create a partial vacuum in the chamber, and at least a second port providing a connection via a second vacuum line between the chamber and a first hand-held instrument to operate the instrument when a partial vacuum is applied through the second vacuum line; and
   at least one insert secured to the housing at one of the hand piece holders and defining an arcuate slot of a second diametric size smaller than the first diametric size for selectively accommodating a hand-held instrument having a smaller than maximum diametric dimension.

2. The instrumentation delivery unit of claim 1 wherein the first and second members include a fastening mechanism for releasably holding the members together when the housing is configured in its closed position and enabling separation of the members to permit access to the interior of the chamber when the housing is configured in its open position.

3. The instrumentation delivery unit of claim 1 further including a filter element in the chamber to prevent debris from exiting the chamber through the first portal.

4. The instrumentation delivery unit of claim 3 wherein the housing includes a vessel defining a portion of the chamber and into which debris may be collected.

5. The instrumentation delivery unit of claim 4 wherein the housing includes a lid positioned along an interior surface of the first member and the vessel is positioned along an interior surface of the second member to engage the lid in a sealing relationship to sustain the partial vacuum in the chamber.

6. The instrumentation delivery unit of claim 5 wherein the lid is pivotally connected to the housing such that rotation movement of the lid provides access to the vessel.

7. The instrumentation delivery unit of claim 1 wherein the housing comprises first and second members configurable in an open position and a closed position, and with the insert being received between the first and second members when the housing is in its open position and held in position between the members when the housing is in its closed position.

8. The instrumentation delivery unit of claim 7 wherein the insert has a first shoulder region at a first end thereof which is engaged by one of the housing members when the housing is in its closed position.

9. The instrumentation delivery unit of claim 8 wherein the insert has a second shoulder region along at second end thereof which is engaged by the other of the housing members when the housing is in its closed position.

10. The instrumentation delivery unit of claim 8 including a plurality of inserts having first and second shoulder portions of generally the same size, but having slots of varying diametric size.

11. The instrumentation delivery unit of claim 8 wherein with the housing in its open position, the inserts can be moved between different hand piece holder locations, so that a user can modify the arrangement of inserts on the housing for hand-held instrument preferences and to change instrument locations.

12. An instrumentation delivery unit of the type which supports hand-held instruments used in dental procedures, comprising:
a housing including a plurality of members configurable in multiple positions, including first and second housing members which, when brought together, provide a sealed chamber therein and, when separated, permit access to an interior region of the chamber, the chamber including a first portal suitable for connection to a vacuum line to create a partial vacuum in the chamber, and at least a second portal providing a connection via a second vacuum line between the chamber and one of the hand-held instruments to effect operation thereof when a partial vacuum is extended through the second vacuum line,
the housing including, along an exterior portion thereof, a plurality of hand piece holders each of an initial diametric size for receiving hand pieces up to a maximum diametric dimension, with the hand piece holders being formed along two adjoining ones of the housing members, said two adjoining housing members configured to secure an insert between one another to effect receipt in one of the hand piece holders; and
at least one insert secured to the housing at one of the plurality of hand piece holders and defining an arcuate slot of a second diametric size smaller than the first diametric size for selectively accommodating a hand-held instrument having a smaller than maximum diametric dimension.

13. The instrumentation delivery unit of claim 12 wherein the first and second housing members are of different configuration from the said two adjoining housing members.

14. The instrumentation delivery unit of claim 12 further including a plurality of inserts of varied size diametric size, each interchangeably positionable in multiple ones of the hand piece holders to selectably accommodate a hand piece having a smaller than maximum diametric dimension.

15. The instrumentation delivery unit of claim 12 wherein the housing includes a center portion comprising the first and second housing members with the chamber formed therein and multiple side portions having the hand piece holders formed along surfaces thereof, wherein the side portions are each positioned adjacent the center portion so that the hand piece holders formed in each side portion extend into one of the first and second housing members.

* * * * *